(12) United States Patent
Haynes et al.

(10) Patent No.: US 7,303,303 B1
(45) Date of Patent: Dec. 4, 2007

(54) LIP LIGHT

(76) Inventors: Derek Haynes, 25080 Goldcrest Dr., Bonita Springs, FL (US) 34134; Stuart M. Jenkins, 105 Aldwick Rd., Bognor Regis, West Sussex (GB) PO21 2NY ( * ) Notice: Subject to any disclaimer, the term of this patent is extended or adjusted under 35 U.S.C. 154(b) by 0 days.

(21) Appl. No.: 11/390,877

(22) Filed: Mar. 28, 2006

Related U.S. Application Data

(60) Provisional application No. 60/665,194, filed on Mar. 28, 2005.

(51) Int. Cl.
*F21V 21/84* (2006.01)
(52) U.S. Cl. .................. 362/105; 362/394; 381/367
(58) Field of Classification Search ........ 362/105–106, 362/394; 381/367, 361
See application file for complete search history.

(56) References Cited

U.S. PATENT DOCUMENTS

| 5,083,246 | A | 1/1992 | Lambert |
| 5,951,141 | A | 9/1999 | Bradley |
| 6,824,265 | B1 * | 11/2004 | Harper ........................ 351/158 |
| 6,918,678 | B2 | 7/2005 | McClanahan |
| 2005/0105285 | A1 | 5/2005 | Maden |
| 2006/0139907 | A1 * | 6/2006 | Yen ............................. 362/85 |

\* cited by examiner

*Primary Examiner*—Thomas M. Sember
*Assistant Examiner*—Julie A. Shallenberger
(74) *Attorney, Agent, or Firm*—John P. McGonagle

(57) ABSTRACT

An illuminating device in combination with a microphone boom attached to a helmet worn by an operator. The illumination device is actuated by either lip action or push button. The brightness of the selected illumination is changeable by means of a potentiometer thumbwheel. The illumination device provides one spot and three flood light emitting diodes which may individually or as a group switched on or off. The illumination device has a universal clamping system permitting attachment to single or double boom microphone.

4 Claims, 5 Drawing Sheets

LIP LIGHT

CROSS-REFERENCE TO RELATED APPLICATIONS

Applicants claim the priority benefits of U.S. Provisional Patent Application No. 60/665,194, filed Mar. 28, 2005.

BACKGROUND OF THE INVENTION

This invention relates to portable illuminating devices, and more particularly to a lip actuated illuminating device.

There are presently on the market aviator's and military vehicle operator's night vision systems which enable pilots to fly helicopters or drive armored vehicles even in the darkest of night conditions without illumination. However, in order to be able to use the available night vision systems it is necessary to turn off the illuminating means for the various gauges used in the cockpit of a helicopter or vehicle. The reason for this is that the illuminating devices are so bright that the night vision goggles used would be blown out or otherwise adversely affected or compromised by the overloading of the illumination from the gauges. That is, the illumination from the gauges, when taken in directly by the goggles, overloads the light amplification circuitry in the goggles and thereby turns off the goggles.

Accordingly, an important problem for pilots and vehicle operators using a night vision system at night is that various gauges that must still be monitored during flight or vehicle operation cannot be seen in the dark. Also, even if the night vision goggles are turned off or taken off, it is still imperative that the illumination of the gauges does not enable the aircraft or vehicle to be seen at night from outside the aircraft or vehicle when used clandestinely.

There is, therefore, a need to provide illumination for pilots or armored vehicle personnel in confined spaces such as the cockpit of an aircraft or interior of an armored vehicle where the instrument lights provide reduced or impaired vision when used in conjunction with night vision glasses. Since the aircraft or vehicle requires two hands to operate, it is also important that such an illumination device be attached to the helmet mounted microphone of the pilot or vehicle operator for actuation by the lip or tongue.

SUMMARY OF THE INVENTION

The present invention provides an apparatus for illuminating a portion of the interior of an aircraft or vehicle. The apparatus comprises an LED unit worn by the pilot or vehicle operator for producing a light beam which is sufficiently bright so that an object located within the beam may be readily distinguished, yet is sufficiently low that it will not adversely affect the operation of a night vision imaging system.

The present invention extends the function, convenience and application beyond all other currently available lip lights. It allows the unit illumination to be actuated by either lip action or push button mode. Additionally, the present invention allows the brightness of the selected illumination to be changed using a potentiometer wheel. The present invention provides four LEDs which may all be switched on or off at the same time providing the best range of operating flexibility for the prevailing operating conditions. The present invention has a memory function which will bring the unit back into operation at its last used setting. The present invention's clamping system permits the invention to be easily attached to single or two boom microphone supports with a universal joint system which allows the invention light head to be easily positioned to suit each operator's personal needs.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

DETAILED DESCRIPTION OF THE INVENTION

Figure 1:
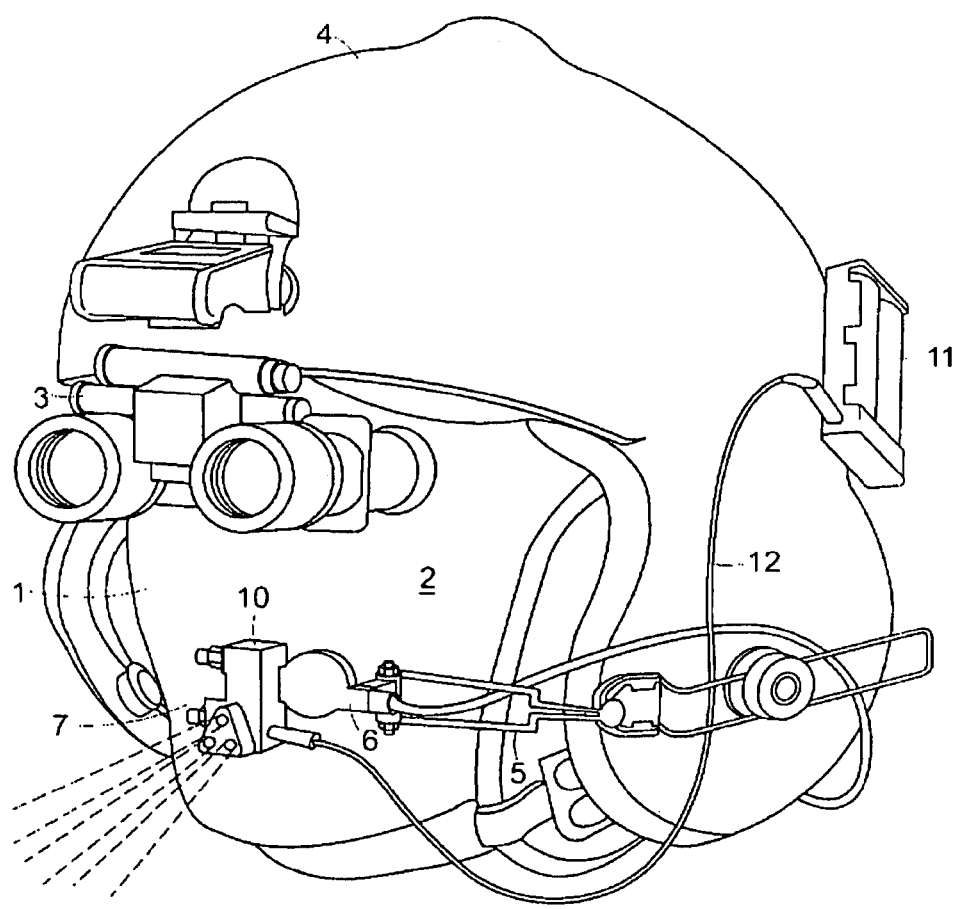
FIG. 1 is a view of the invention attached to an operator's microphone.
Figure 2:
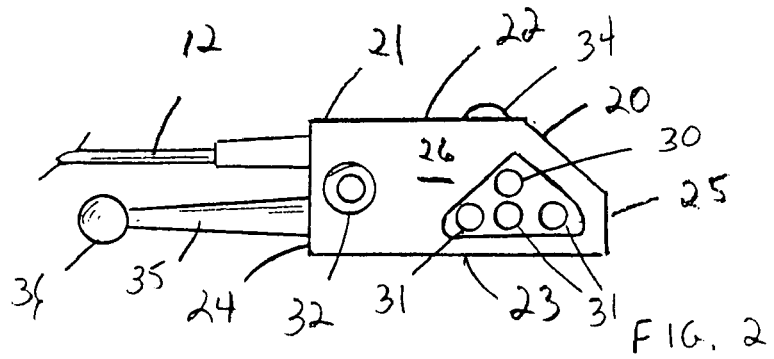
FIG. 2 is a front view of the light head.
Figure 3:
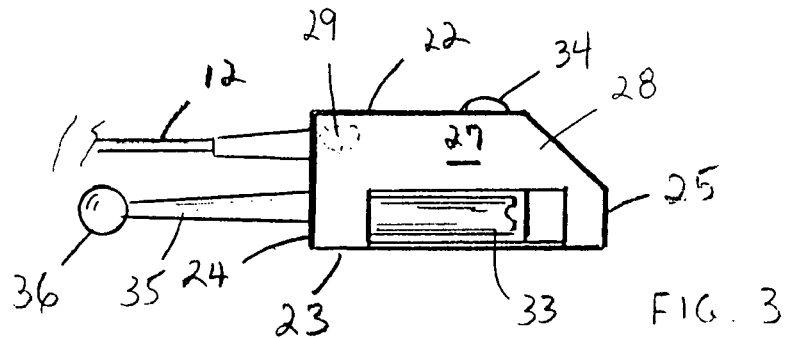
FIG. 3 is a rear view thereof.
Figure 4:
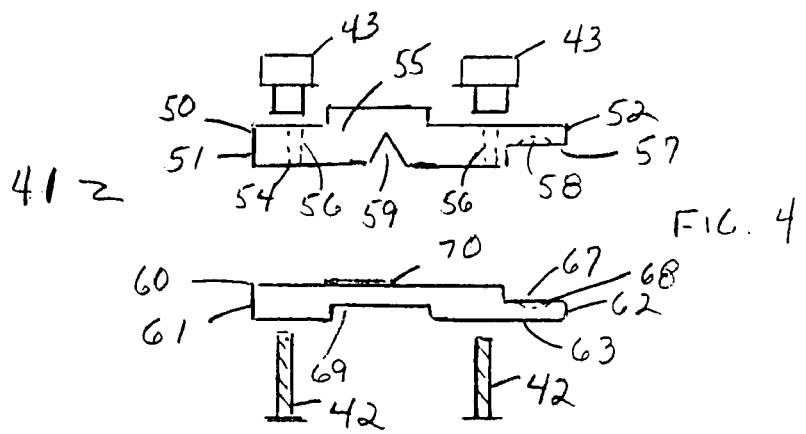
FIG. 4 is a an exploded view of the universal joint system clamping module.
Figure 5:
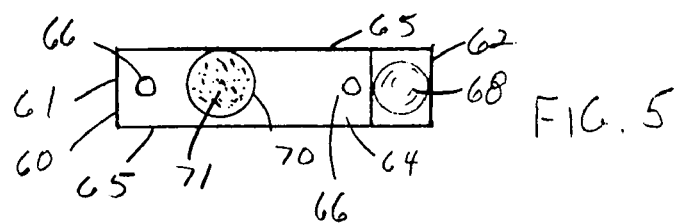
FIG. 5 is a top view of the rearward clamping element.
Figure 6:
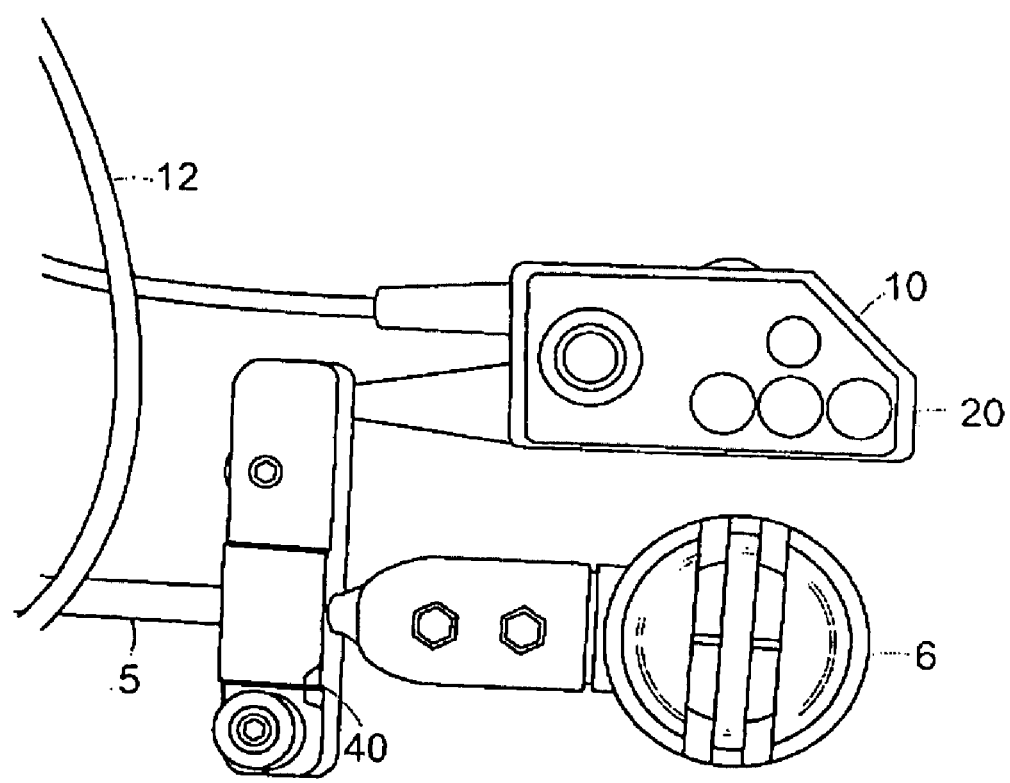
FIG. 6 is a view of the lip light attached to a microphone boom.

Referring to the drawings in detail wherein like elements are indicated by like numerals, there is shown a lip light 10 constructed according to the principles of the present invention. The lip light 10 is comprised of a light head 20 attached to a universal joint system 40 and interconnected by means of a wire 12 with a battery pack 11. The battery pack 11 may be conveniently removably attached to the helmet 4. The lip light 10 is attached to a microphone boom 5 attached to a helmet 4 worn by an operator 1. As may be best seen in FIG. 1, the operator 1 has night vision goggles 3 attached to his helmet 4 and positioned in front of his face 2. The microphone boom 5 is position so that a microphone 6 is positioned adjacent the operator's mouth area 7.

The light head 20 is comprised of a housing 21 having a nominal top 22, bottom 23, connection side 24, free side 25, front 26, rear 27, and exterior surface 28, said top, bottom, sides, front, and rear defining a housing interior 29, said sides 24, 25 defining a housing longitudinal axis. The housing rear 27 is defined as that portion of the housing 21 closest to the operator's face 2, and the housing front 26 as that portion of the housing 21 farthest from the operator's face 2. The housing front 26 has one light emitting diode (LED) spot light 30 and three LED flood lights 31 mounted thereon and projecting through said exterior surface 28. Other embodiment of the invention may have more or less lights. The housing front 26 has a push button 32 switch mounted thereon. The housing rear 27 has a lip/tongue actuated switch 33 mounted thereon. The housing top 22 has an optional potentiometer wheel 34 attached thereto said wheel 34 substantially contained within the housing interior 29 but partially protruding through the housing exterior 28.

The light head housing connection side 24 has an elongated rod 35 with a longitudinal axis positioned substantially co-extensive with the housing longitudinal axis. The elongated rod terminates in a spherical protrusion 36. An electrical cord 12 is also joined to the housing interior 29 through the housing connection side 24.

The universal joint system 40 is comprised of a clamping module 41 pivotally attached to said housing spherical protrusion 36. The clamping module 41 is comprised of a forward clamping element 50 and a rearward clamping element 60.

The rearward clamping element 60 has a first end 61, a second end 62, an exterior surface 63, an interior surface 64 and two opposite sides 65. The interior surface 64 is defined as that portion of the rearward clamping element 60 facing forward clamping element 50. The interior surface 64 has a flat channel 67 formed therein at the second end 62 extending from side 65 to side 65. The channel 67 has a rounded depression 68 formed therein. The rearward clamping element 60 has two apertures 66 formed therein, one aperture near to said first end 61 and the second aperture adjacent said channel 67, said apertures extending from the exterior surface 63 through the interior surface 64. The exterior surface 63 has a rectangular channel 69 formed therein adjacent the first end aperture 66 and extending a designated distance toward the second end 62.

The forward clamping element 50 has a first end 51, a second end 52, an exterior surface 53, an interior surface 54 and two opposite sides 55. The interior surface 54 is defined as that portion of the forward clamping element 50 facing the rearward clamping element 60. The interior surface 54 has a flat channel 57 formed therein at the second end 52 extending from side 55 to side 55. The channel 57 has a rounded depression 58 formed therein. The forward clamping element 50 has two apertures 56 formed therein, one aperture near to said first end 51 and the second aperture adjacent said channel 57, said apertures extending from the exterior surface 53 through the interior surface 54. The forward clamping element interior surface has a second channel 59 formed therein between said apertures 56. The second channel 59 extends from side to side and has a side-to-side V-shaped profile.

The clamping module has two threaded screws 42, each inserted into the rearward element apertures 66 from the exterior surface 63 through and out the interior surface 64. The forward clamping element 50 is joined to the rearward clamping element 60 by engaging the screws 42 with the forward clamping element apertures 56. Each screw 42 is threadingly engaged by a threaded nut 43 on the portion of the screw protruding past the forward clamping element exterior surface 53.

The clamping module 41 receives the spherical protrusion 36 between the clamping elements' second ends 52, 62 into the channel areas 57, 67 wherein the spherical protrusion 36 is seated between the rounded depressions 58, 68. The boom microphone 5 is sandwiched between the clamping element interior surfaces 54, 64 in the interior surface areas between the apertures 56, 66. The forward clamping element second channel 59 provides means for securely attaching the clamping module 41 to a single boom microphone. An optional patch 70 with a roughened surface 71 may be attached to the rearward clamping element interior surface 64 between the apertures 66 for increased gripping action. The threaded nuts 43 provides means for variable tightening on the microphone boom 5 and the light head housing spherical protrusion 36. The present invention universal joint system 40 allows the invention light head 20 to be easily positioned to suit each operator's personal needs.

Figure 7:
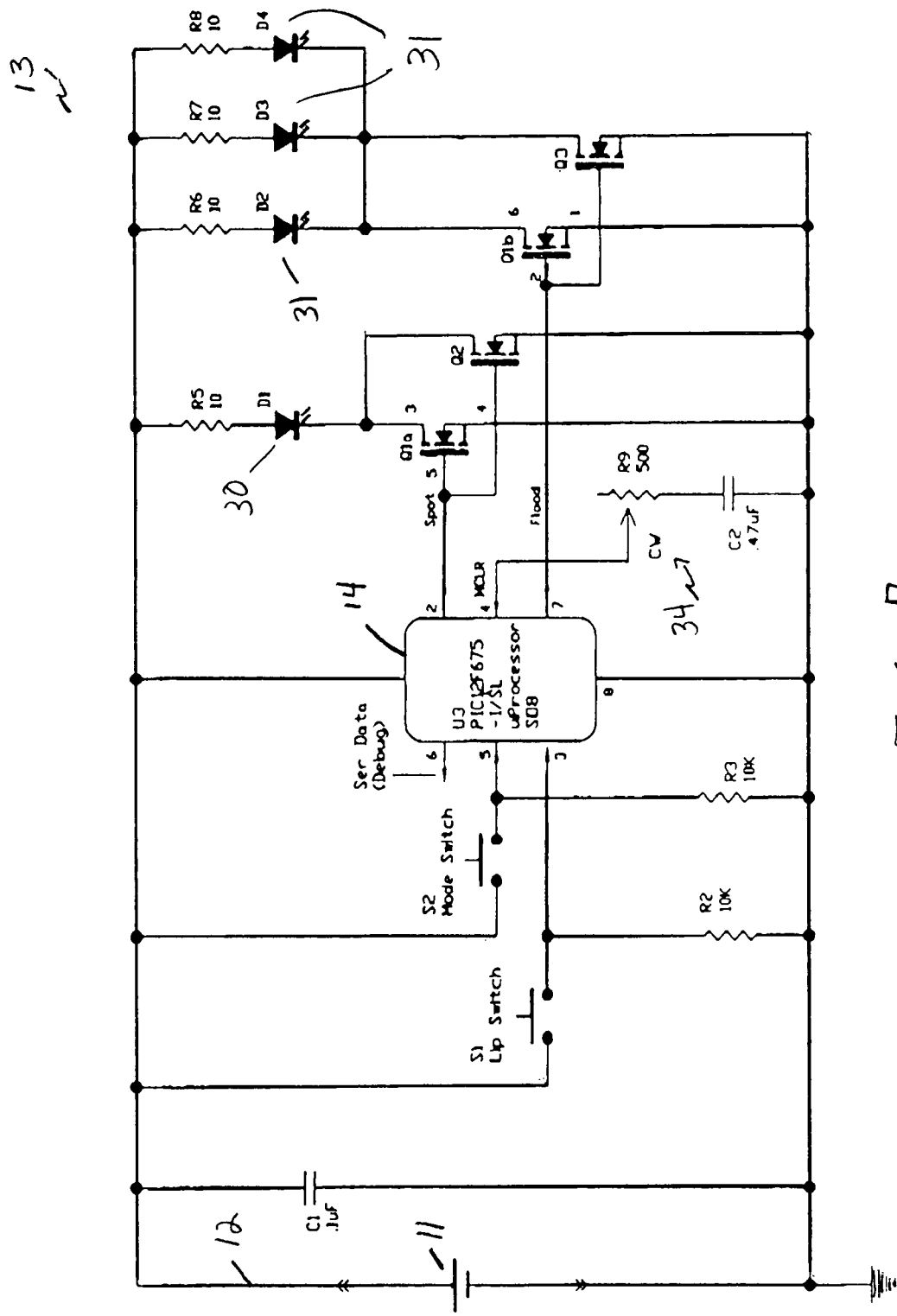
FIG. 7 is a schematic diagram of one embodiment of the electrical circuitry of the invention.
Figure 8:
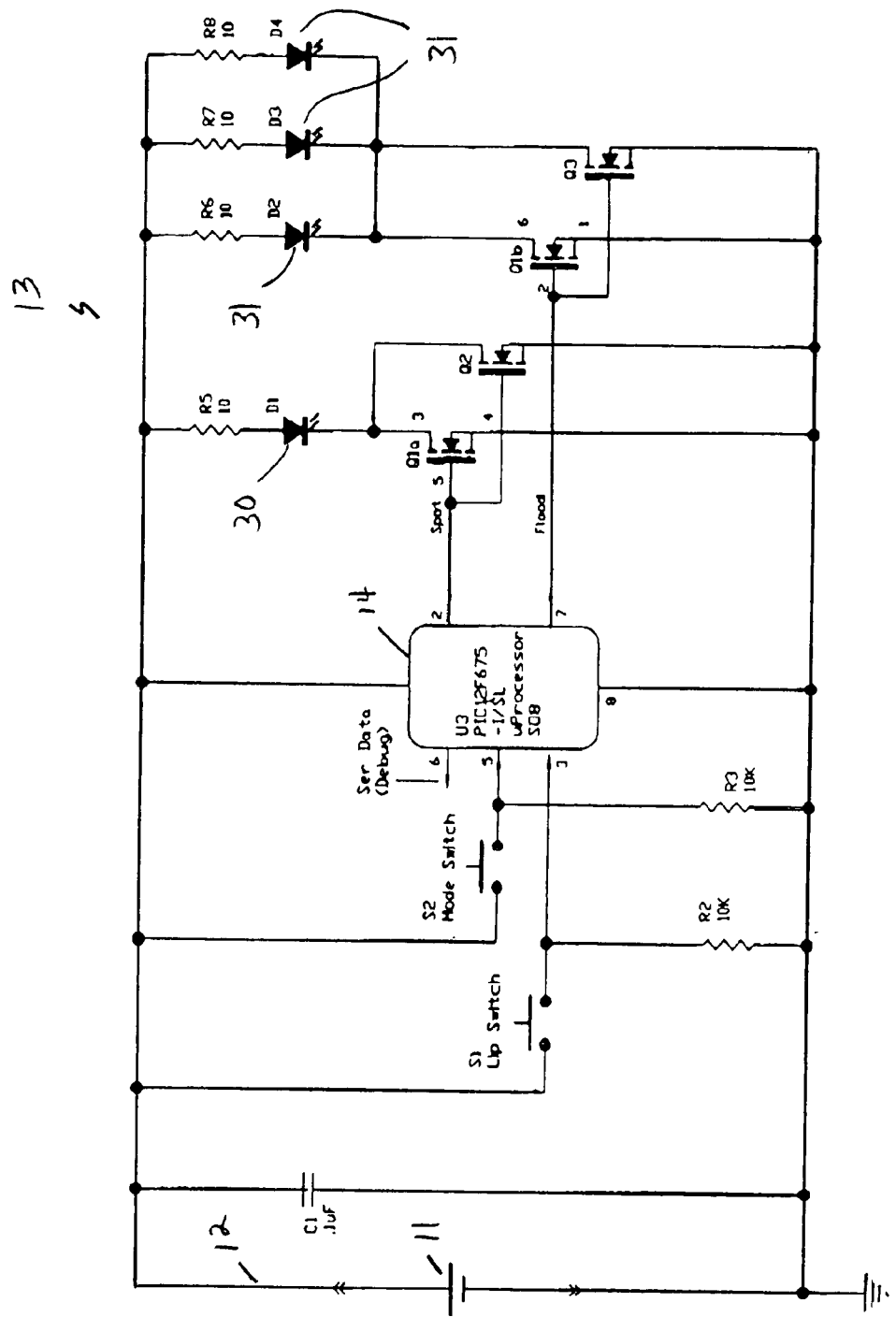
FIG. 8 is a schematic diagram of another embodiment of the electrical circuitry of the invention.

Referring more particularly to FIGS. 7 and 8, there is shown schematic diagrams of two embodiments of the electrical circuitry of the invention. The electrical circuitry 13 is contained within the light head housing interior 29. The circuitry 13 has as its heart a microprocessor 14 electrically connected to the lip/tongue switch 33, indicated electronically as S1, and the push button mode switch 32, indicated electronically as S2. The microprocessor 14 is electrically connected to the LED spot light 30, indicated electrically as R5 and driven by Q1a and/or Q2. The microprocessor 14 is also electrically connected to the three LED flood lights 31, indicated electrically as R6, R7, and R8, and driven by Q1b and/or Q3. The electrical circuitry 13 is powered by two AA batteries in a battery pack 11 electrically interconnected to the circuitry 13 by the electrical cord 12.

In the first embodiment shown in FIG. 7, provision is made for directly changing the brightness of the selected illumination by using a potentiometer wheel 34 indicated electronically by CW and R9 connected to the microprocessor. The alternate circuit embodiment shown in FIG. 8 eliminates the potentiometer 34 and relies instead on the microprocessor 14 to modulate the LEDs thereby providing the appearance of brighter or dimmer settings.

In operation the lip switch 33 provides two modes of operation: "latching" and "momentary." Commencing with the LED's OFF, tapping the lip switch 33 quickly will switch the LED's ON and remain "latched" ON after the switch has been released. Pressing the lip switch 33 again will turn the LED's OFF. Alternatively, if the lip switch 33 is held down for approximately one second or more when turning the LED's ON, the circuitry goes into the "momentary" mode and the LEDs will turn OFF when the switch is released.

The LED Mode Switch 32 operates with progressive looping action. Each time the switch is pushed, it will advance the illumination mode. If starting with one spot LED 30 on, the next push of the Mode Switch 32 will bring three flood LEDs 31 on; the next all LED's 30, 31 ON; and then following returning to the beginning of the loop of one spot LED 300N. The lip light 20 "remembers" the last mode setting when powered down and will come ON with that setting the next time it is powered up again.

A thumbwheel potentiometer 34 may be provided which permits direct operator adjustment of the LED illumination brightness. At the lowest setting, the LED provides a fain glow to indicate that the unit is ON and that the batteries are being drained.

In an alternate embodiment of the invention, the LED brightness adjustment function is integrated into a LED illumination Mode Selection switch 32. In this version, the function and operation of the Lip Switch 33 remains unchanged from the above description. That is, a quick tap of the lip switch 33 will result in an alternating ON/OFF illumination action of the LEDs. The first tap of the Lip Switch 33 will cause the LEDs to illuminate and remain ON. The next tap will turn the LEDs OFF. However, if the Lip Switch 33 is held longer than about ⅓ of a second, the LEDs will extinguish when the switch is released.

The operation of the Mode Switch 32 in this alternate embodiment acquires some of the characteristics of the Lip Switch 33. That is, quick taps of less than ½ second in duration will cause the illumination Mode to be advanced in a loop from the Spot LED Mode, to three Flood LEDs, to all four LEDs together, back to the Spot LED again, and so forth. The LED illumination mode switching action occurs on the release stroke of the Mode Switch 32 tap.

Holding the Mode Switch 32 down for a longer period (approximately ½ second) changes the Mode Switch action to the adjustment of LED brightness. After the ½ second period has elapsed, a continued hold of the Mode Switch will result in a sweeping action of the LED brightness between the extremes of brightness and dimness, and this sweeping action will continue as long as the Mode Switch 32 is kept pressed. The moment of release of the Mode Switch is used to select the desired LED illumination brightness setting.

The following characteristics have been designed into the LED brightness adjustment feature to help with ergonomic convenience. The direction of the brightness change will always resume in the same direction as the last time that a brightness adjustment had been made. That is, if the brightness had been increasing that last time the brightness was adjusted, the next time the brightness will begin sweeping in the direction of increasing brightness. Similarly, if the brightness had been decreasing, it will resume by decreasing. When either the maximum or minimum brightness is reached, the lip light LEDs will blink to indicate to the user that this has occurred. The maximum or minimum brightness will continue to be held constant for about ⅓ of a second to facilitate capturing those settings. Release of the mode switch 32 after making a brightness adjustment will not effect the LED illumination mode.

The brightness setting as well as the LED illumination modes are stored in non-volitile memory within the microprocessor 14 and will return to the last setting the next time the Lip Light 10 is turned on with the Lip Switch 33. These brightness and illumination mode settings are also not affected by power removal or battery changes.

It is understood that the above-described embodiment is merely illustrative of the application. Other embodiments may be readily devised by those skilled in the art which will embody the principles of the invention and fall within the spirit and scope thereof.

We claim:

1. An illuminating device in combination with a microphone boom attached to a helmet worn by an operator, said microphone boom positioned so that an attached microphone is positioned adjacent an operator's mouth area, comprising:
    a light head comprised of a housing having a top, a bottom, a connection side, a free side, a front, a rear, and an exterior surface, said top, bottom, sides, front, and rear defining a housing interior, said sides defining a housing longitudinal axis, said housing rear being that portion of the housing closest to the operator's mouth area, and the housing front being that portion of the housing farthest from the operator's face;
    an elongated rod attached to the housing connection side and having a longitudinal axis positioned substantially co-extensive with the housing longitudinal axis, said elongated rod terminating in a spherical protrusion;
    a plurality of light emitting diodes mounted on said housing front;
    means for changing the brightness of light emitting from said light emitting diodes;
    a push button mode switch on said housing front;
    a lip and tongue actuated switch on said housing rear;
    a universal joint system interconnecting said light head to said microphone boom, said universal joint system comprised of a clamping module pivotally attached to said elongated rod spherical protrusion;
    an electrical circuit in said housing interior, said electrical circuit containing a microprocessor electrically connected to the lip and tongue actuated switch, the push button mode switch and the plurality of light emitting diodes, said microprocessor having a nonvolatile memory;
    a battery pack located external to the housing and electrically interconnected to said electrical circuit;
    wherein the lip and tongue actuated switch provides individual and group ON-OFF control of the light emitting diodes;
    wherein the push button mode switch provides progressive ON-OFF control of the light emitting diodes;
    wherein the clamping module is comprised of:
        a forward clamping element having a first end, a second end, an exterior surface, an interior surface and two opposite sides, said forward clamping element interior surface being that portion of the forward clamping element facing the rearward clamping element, said forward clamping element interior surface having a flat channel formed therein at the second end extending from side to side, said forward clamping element flat channel having a rounded depression formed therein, said forward clamping element having two apertures formed therein, one aperture near to said first end and the second aperture adjacent said forward clamping element flat channel, said apertures extending from the forward clamping element exterior surface through the forward clamping element interior surface, said forward clamping element interior surface having a second channel formed therein between said apertures, said forward clamping element second channel extending from side to side and having a side-to-side V-shaped profile;
        a rearward clamping element having a first end, a second end, an exterior surface, an interior surface and two opposite sides, said rearward clamping element interior surface being that portion of the rearward clamping element facing forward clamping element, said rearward clamping element interior surface having a flat channel formed therein at the second end extending from side to side, said channel having a rounded depression formed therein, the rearward clamping element having two apertures formed therein, one aperture near to said first end and the second aperture adjacent said channel, said apertures extending from the exterior surface through the interior surface, said rearward clamping element exterior surface having a rectangular channel formed therein adjacent the first end aperture and extending a designated distance toward the second end;
        two threaded screws, each screw inserted into the a rearward element aperture from the rearward element exterior surface through and out the rearward element interior surface;
    wherein the forward clamping element is joined to the rearward clamping element by engaging the screws with the forward clamping element apertures, each screw being threadingly engaged by a threaded nut on a portion of the screw protruding past the forward clamping element exterior surface.

2. An illumination device as recited in claim 1, wherein: the clamping module is adapted to receive the spherical protrusion between the clamping elements' second ends into the channel areas wherein the spherical protrusion is seated between the rounded depressions; the boom microphone is sandwiched between the clamping element interior surfaces in the interior surface areas between the apertures, said forward clamping element second channel providing means for securely attaching the clamping module to a single boom microphone.

3. An illumination device as recited in claim 2, further comprising:
    a patch with a roughened surface attached to the rearward clamping element interior surface between the apertures for increased gripping action.

4. An illumination device as recited in claim 2, wherein: the battery pack is removably attached to the helmet.

* * * * *